United States Patent [19]
Pittenger

[11] Patent Number: 5,827,740
[45] Date of Patent: Oct. 27, 1998

[54] ADIPOGENIC DIFFERENTIATION OF HUMAN MESENCHYMAL STEM CELLS

[75] Inventor: Mark F. Pittenger, Severna Park, Md.

[73] Assignee: Osiris Therapeutics, Inc., Baltimore, Md.

[21] Appl. No.: 700,753

[22] Filed: Jul. 30, 1996

[51] Int. Cl.$^6$ ................................ C12N 5/08; C07J 1/00; A61K 45/00
[52] U.S. Cl. .................... 435/372; 435/366; 435/377; 435/405; 514/46; 514/171; 514/261; 514/263; 514/415; 532/2
[58] Field of Search ..................... 435/377, 372, 435/366, 405; 424/572, 574; 514/171, 46, 261, 263, 415; 532/2

[56] References Cited

U.S. PATENT DOCUMENTS 5,486,359  1/1996  Caplan et al. .................... 424/93.7

OTHER PUBLICATIONS

Merck & Co. In Merck Index: 10th edition. Merck & Co. Rahway, NJ. pp. 362, 693–694, 1983.
Lehmann, JM et al. J. Biol. Chem. 270(22): 12953–12956, Jun. 2, 1995.
Wang, EA et al. Growth Factors. 9(1): 57–71, Jan. 1993.
Grigoriadis, AE et al. J. Cell Biol. 106(6): 2139–2151, Jun. 1988.
Estrov, Z et al. Experimental Hematology. 11(9): 802–809, Oct. 1983.
DeFelici, M et al. CIBA Foundation Symposium. 182: 140–153, 1994.
Loffler, G et al. Klinische Wochenschrift. 65(17): 812–817, Sep. 1, 1987.

*Primary Examiner*—David Saunders
*Assistant Examiner*—F. Pierre VanderVegt
*Attorney, Agent, or Firm*—Charles J. Herron; Elliot M. Olstein

[57] ABSTRACT

A composition which comprises human mesenchymal stem cells which have the potential to differentiate into cells of more than one connective tissue type and a composition which induces cells from the mesenchymal stem cell population to differentiate into the adipogenic lineage, and a process for inducing such differentiation. The composition for inducing such differentiation comprises a glucocorticoid and a compound which stimulates cAMP production or inhibits cAMP degradation (such as a phosphodiesterase inhibitor). The process can further include isolating the adipocytes from remaining hMSCs.

14 Claims, 9 Drawing Sheets

ADIPOGENIC DIFFERENTIATION OF HUMAN MESENCHYMAL STEM CELLS

This invention relates to adipocytes and more particularly to producing adipocytes from human mesenchymal stem cells.

Adipose tissue provides an energy storage reserve for the body in the form of triglycerides and this tissue can release free fatty acids when caloric intake falls below metabolic needs. In response to increased dietary intake, the body will normally automatically increase energy expenditure through activity to maintain an energy balance. Energy can also be released as heat. Adipose tissue is intimately involved in the maintenance of body temperature through brown adipose tissue and energy storage through white adipose tissue. There are normal energy regulation pathways that balance dietary intake with metabolic activity largely mediated through the hypothalamus. It is now also apparent that the adipocyte plays an active role in this process and likely produces molecules that serve to feed back and effect regulation of triglyceride metabolism.

The two types of adipose tissue, brown and white, carry out very different roles in the body. White adipose is designed to store excess caloric intake while brown adipose tissue uses a unique system to syphon off excess calories and use it to generate body heat. The heat is generated in the mitochondria of brown adipose where oxidation of substrate is utilized to create a hydrogen ion gradient that is then collapsed in a regulated fashion generating heat instead of ATP. It has been shown that transgenic animals that lack brown adipose maintain efficient metabolism, are obese and continue to overeat (Lowell et al, 1993). Other rodent studies have also shown a link between obesity, continued overeating and a sensitivity to cold, suggesting a connection to the sympathetic nervous system (Friedman and Leibel, 1992).

Imbalance in energy metabolism in the body leads to several diseased states, most notably obesity and obesity-induced diabetes and these can be described as dysfunctions of energy storage tissues. A mutation in mice that leads to obesity was identified in 1950 (Ingalls et al., 1950) and the gene was recently identified by positional cloning. The product of the ob gene is a 16,000 mw protein named leptin or OB protein. Leptin is produced only by adipocytes and is a hormone which regulates the hypothalamus. A mutation has been identified in the of mouse that results in premature termination of mRNA translation such that no functional leptin protein is made (Zhang et al. 1994). The role of leptin in regulation of lipid metabolism is an area of intense research. Recent published investigations include studies of the upstream promoter elements found adjacent to the ob gene which have been shown to bind C/EBP (or CCAAT/enhancer binding protein) (Yeh et al, 1995 and Hwang et al., 1996). Having a model experimental system for in vitro adipogenesis of human cells would provide for discoveries in this area.

Recently it has been reported that leptin may serve as a hormone that regulates fertility and may be the link between appropriate body weight and reproductive physiology (Chehab et al. 1996). Both underweight and overweight women have difficulty in conceiving and this is likely associated with hormonal imbalance in the body of these individuals. The connection between body weight, fertility and the leptin produced by adipocytes has been suspected and now tested in mice. When obese mice, which normally do not produce offspring without transplanting the ovaries to surrogate females, were injected with leptin, there body weight fell dramatically and they were able to give birth to their own litters (Chehab et al, 1996).

A variety of cell types have been shown to produce lipid containing vesicles under specific culture conditions. For example, mouse 3T3-L1 cells derived from NIH 3T3, an immortalized mouse cell line, can be grown and cultured as a fibroblastic cell. However, after exposure to dexamethasone and methyl-isobutylxanthine, the cells undergo differentiation which results in the production of intracellular lipid-containing vacuoles (Spiegelman and Green, 1981). Rat marrow stromal cells have been shown to undergo both osteogenic and adipogenic differentiation when cultured with fetal calf serum and dexamethasone, but the predominating cell type varies depending on conditions (Beresford et al., 1992). Specifically, when the steroid analog dexamethasone was present throughout the time course of culture, osteogenesis was favored; but when dexamethasone was present only during secondary culture, the adipogenetic pathway predominated as evidenced by lineage specific markers and cytological observation. Mouse derived CH3 10T1/2 cells are a multipotential cell line that, when treated with 5-azacytidine, undergoes terminal differentiation into adipocytes, myocytes and chondrocytes. The 5-azacytidine causes inhibition of DNA methylation and thus causes the activation of a few genes responsible for commitment to these lineages (Konieczny and Emerson, 1984).

In accordance with one aspect of the present invention, there is provided a composition and method for inducing human mesenchymal stem cells to preferentially differentiate into the adipogenic lineage, i.e., to differentiate into adipocytes.

Applicant has found that mesenchymal stem cells and in particular human mesenchymal stem cells (hMSC) can be directed to differentiate into adipocytes by treating the human mesenchymal stem cells with (i) a glucocorticoid and (ii) a compound which elevates intracellular cAMP levels by either upregulating cAMP production or by inhibiting degradation of cAMP; in particular a compound which inhibits compound(s) which degrade cAMP.

In a preferred aspect, the human mesenchymal stem cells are treated with a glucocorticoid and a compound which inhibits the activity of a compound which degrades cAMP; in particular a phosphodiesterase inhibitor. The cells are subsequently cultured in media containing insulin and fetal bovine serum.

Human mesenchymal stem cells, as well as their isolation and expansion, have been described in U.S. Pat. No. 5,486,359. As known in the art, human mesenchymal stem cells are capable of producing two or more different types (lineages) of mesenchymal cells or tissues and in particular connective tissue. The present invention provides a method for generating adipocytes from primary human mesenchymal stem cells (hMSCs) in a predictable and reproducible manner. The invention is unique in that it involves human cells in primary and passaged cultures rather than transformed or immortalized cell lines that are predetermined to enter the adipogenic pathway. hMSCs are capable of entering multiple lineages including the osteocytic, chondrocytic, myocytic, tendonocytic and stromogenic lineages and the present invention provides a method and composition for inducing hMSC's to differentiate into adipocytes. In a preferred aspect, in accordance with the present invention, hMSC's are induced to differentiate into essentially only adipocytes, i.e., there is no essential production or commitment to cells of other mesenchymal lineages. The method may also be used for generating adipocytes from MSCs from other species such as rabbit, dog, rat and mouse.

The invention also provides methods to purify the adipocytes to obtain a highly purified population.

The method of the invention for the in vitro differentiation of human mesenchymal stem cells preferably derived from bone marrow into adipoblastic or adipocytic cells is useful to investigators wishing to study this developmental program in human cells in vitro. A better understanding of diseases of energy metabolism including obesity and obesity-related diabetes will also result from studies of the differentiation of mesenchymal stem cells to adipocytes. While a cellular and biochemical basis for obesity has long been suspected, advancements have been slow due to a lack of model systems with biochemical and molecular tools for study. Recent dramatic breakthroughs in the molecular basis of adipogenesis have opened new avenues towards understanding this pathway of mesenchymal cell differentiation, although a human model system such as the one described here has been lacking. The method will also have utility in the isolation and preparation of adipocytes for implantation into a patient for the purpose of tissue augmentation following trauma or cosmetic surgery.

BRIEF DESCRIPTION OF THE DRAWINGS

FIG. 1A shows hMSCs (4×) cultured in normal hMSC media for the same period of time as FIG. 1B. There is no evidence of lipid containing vacuoles and the cells maintain the appearance of fibroblasts at high density. In FIG. 1B are hMSCs that were allowed to become confluent and then maintained in normal media for 10 days prior to adding the Adipogenic Induction media (containing methylisobutylxanthine and dexamethasone) for 48 hrs, and then changed to the insulin-containing adipocyte maintenance media for an additional 2 weeks. The lipid vacuoles are first apparent at about 5–7 days but increase in size and abundance over time.

FIG. 3A shows a culture of hMSCs maintained in normal hMSC culture media alone. The cells grow with a fibroblastic morphology. FIG. 3B shows a similar culture that was treated with Adipogenic Induction media for 48 hours and then with Adipogenic Maintenance media for an additional 14 days with media changes every 3 days. The adipogenic cells, perhaps as many as 30–35% of the cells, are evident as they contain the large refractile lipid vacuoles. FIG. 3C shows a culture of hMSCs that were maintained in the Adipogenic Maintenance media for 14 days but was never subjected to the dexamethasone/methyl isobutylxanthine treatment. The cells maintain a flat morphological appearance with no evident vacuoles. FIG. 3D shows a culture of hMSCs that were treated with normal hMSC media containing 1 µM dexamethasone for 48 hours and then cultured for 14 days in the Adipogenic Maintenance media. The cells are disorganized but show very few, if any, lipid vacuoles. FIG. 3E shows a culture of hMSCs that was treated with normal hMSC media containing 0.5 m. methyl-isobutylxanthine for 48 hours and then was maintained for 14 days in the Adipogenic Maintenance media. The cells retain a flat fibroblastic phenotype. FIG. 3F shows a culture of hMSCs that was treated with a media that induces the cells to differentiate along a osteogenic pathway. This media contains 0.1 µM dexamethasone, 10 mM β-glycerol phosphate and 50 µM ascorbic acid 2-phosphate. The presence of refractile osteoid material is evident but no large lipid vacuoles.

DETAILED DESCRIPTION OF THE PREFERRED EMBODIMENTS

Figure 1A:
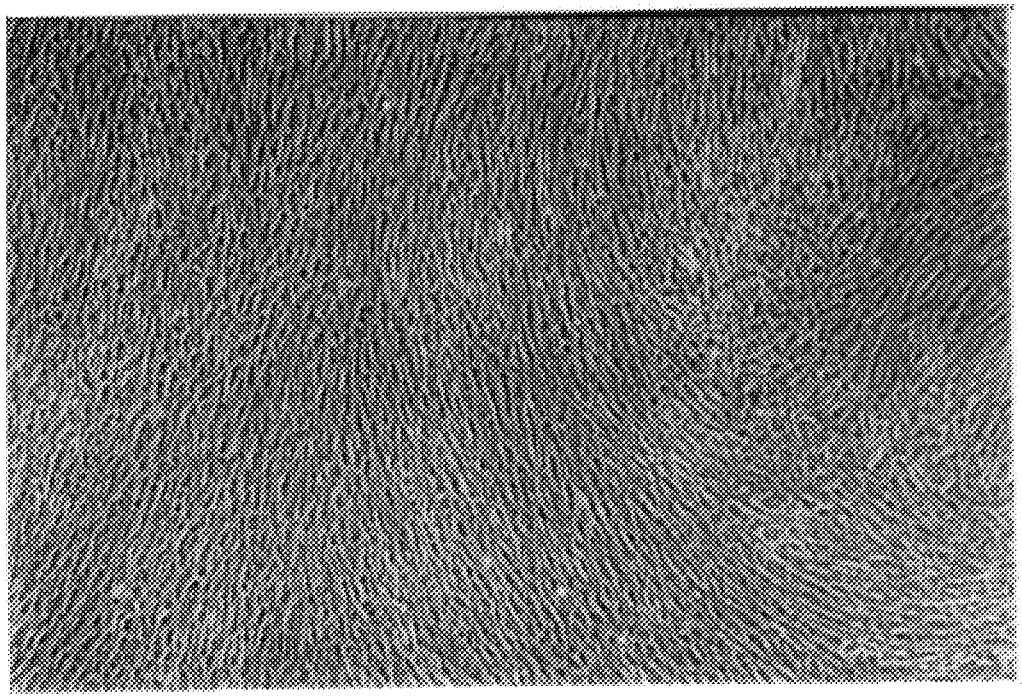
FIGS. 1A–1B show that when human MSCs are treated in accordance with the invention, they undergo differentiation to the adipogenic lineage.

As noted above, one aspect of the invention provides a composition which comprises an isolated, homogeneous population of human mesenchymal stem cells which have the potential to differentiate into cells of more than one mesenchymal tissue type, and a substance which induces cells from the mesenchymal stem cell population to differentiate into the adipogenic lineage.

In a preferred embodiment of this aspect of the invention mesenchymal stem cells are induced to differentiate into the adipogenic lineage by use of a glucocorticoid and a compound which either elevates intracellular levels of cAMP, for example, a cAMP analog or a compound which stimulates production of cAMP or inhibits degradation of cAMP; in particular a phosphodiesterase inhibitor.

Preferred examples of the glucocorticoid are selected from the group consisting of dexamethasone, hydrocortisone, cortisone, etc.

Preferred examples of the substance which elevate intracellular cAMP levels or are cAMP analogs include dibutyryl-cAMP, 8-CPT-cAMP (8-(4)-chlorophenylthio)-adenosine 3', 5' cyclic monophosphate; 8-bromo-cAMP; dioctanoyl-cAMP, Forskolin, etc.

Preferred examples of the substance which inhibits cAMP degradation by inhibiting the activity of phosphodiesterase is selected from the group consisting of methyl isobutylxanthine, theophylline; caffeine, and indomethacin.

The compound which elevates levels of cAMP and the glucocorticoid are used in amounts which are effective to induce hMSCs to differentiate into adipocytes. The cAMP regulating compound and glucocorticoid may be added to the hMSCs separately or in admixture with each other.

In general, the glucocorticoid is used in a concentration from about 0.1 to 10 micromolar, preferably from about 0.5 to 2 micromolar.

When employing a compound which inhibits degradation of cAMP, such a compound is generally employed in a concentration of about 0.1 to 10 millimolar and preferably from about 0.2 to 2 millimolar.

When employing a compound which upregulates cAMP production, such compound is generally employed in a concentration of from about 0.1 to 100 micromolar, preferably from about 0.5 to 10 micromolar.

It is to be understood that the above amounts are representative and the scope of the invention is not to be limited thereby.

Although one of the compounds which is employed to induce hMSCs to differentiate into adipocytes is one which regulates cAMP (either one which is known to upregulate cAMP production or one which prevents degradation of cAMP), the scope of the invention is not limited to any particular mechanism of action. Thus, for example, even though one of the compounds which may be used in the present invention is a phosphodiesterase inhibitor which is known to inhibit degradation of cAMP by inhibiting phosphodiesterase degradation of cAMP, the invention is not limited to a mechanism of action which is dependent upon preventing degradation of cAMP. Thus, for example, the phosphodiesterase inhibitor may be effective for inducing differentiation of hMSCs to adipocytes by a mechanism of action other than inhibiting degradation of cAMP.

Compounds in addition to (i) a glucocorticoid and (ii) a cAMP regulator may be used for inducing hMSCs to differentiate into adipocytes. Thus, for example, in a preferred embodiment insulin is also employed in conjunction with the cAMP regulator and glucocorticoid.

In a preferred embodiment, there is provided a composition for inducing hMSCs to differentiate into adipocytes which is comprised of (i) a glucocorticoid, (ii) a compound which regulates cAMP and in particular a compound which inhibits cAMP degradation such as, a phosphodiesterase inhibitor, (iii) insulin or insulin-like growth factor and (iv) glucose.

The addition of compounds as hereinabove described to induce differentiation of hMSCs to adipocytes in accordance with the invention does not require that all of the treated hMSCs be induced to differentiate into adipocytes. Thus, in accordance with an aspect of the present invention there is produced a composition comprised of human mesenchymal stem cells and adipocytes wherein based on the two components the adipocytes are present in an amount of at least 5 wt. % and preferably at least 15 wt. %. The amount of adipocytes may be up to 50 wt. % or higher, based on the two components.

In accordance with a preferred embodiment, the composition which is generated is essentially free of committed cells of the mesenchymal lineage other than adipocytes. In a particular preferred embodiment, there are less than one percent of committed cells of the mesenchymal lineage other than adipocytes, and more preferably, less than 0.1% and most preferably no committed cells of the mesenchymal lineage other than adipocytes.

Although treatment of hMSCs in accordance with the invention produces a mixture of adipocytes and undifferentiated hMSCs, the produced adipocytes may be recovered from the mixture to produce an isolated population of adipocytes. Representative procedures for recovering adipocytes are described in the examples which form a part of this application.

In accordance with an aspect of the present invention, hMSCs may be treated to induce differentiation into adipocytes in a manner such that such differentiation is effected in vitro or in vivo.

Thus, for example, hMSCs may be admixed with compounds as hereinabove described which induce differentiation into hMSCs and the resulting mixture employed in vivo to induce differentiation to adipocytes in vivo. Thus, for example, the mixture without culturing in vitro for a period of time to induce differentiation in vitro may be employed in a suitable matrix (for example of the type hereinafter described) to induce differentiation of the hMSCs to adipocytes in vivo.

Thus, in accordance with an aspect of the present invention there is provided a composition comprised of human mesenchymal stem cells, a glucocorticoid and a cAMP regulator (a compound(s) which upregulates cAMP production or inhibits cAMP degradation). Such a composition may be employed to produce adipocytes in vitro or may be employed to induce differentiation of hMSCs in vivo.

The ability to generate large percentages of adipogenic cells from a population of hMSCs will allow greater numbers of cells for implantation or research studies. Fewer hMSCs would be needed as starting material. By repeating the adipogenic induction step more times, it should be possible to induce most of the hMSCs in a population to adipocytes. In the case where there is a mixture of cells, adipogenic hMSCs can easily be isolated by their buoyant density. The isolation of a highly enriched population of adipocytes from cultured hMSCs will also allow for a detailed characterization of the adipocyte phenotype.

The adipocytes can be used with a variety of materials to form a composition for purposes such as reconstructive surgery. The cells may be combined with a biomatrix to form a two dimensional or three dimensional material as needed. Surgeons routinely use fat pads and fatty tissues from remote sites to build up an area where tissue has been removed. This often involves a separate procedure with its inherent risks. As an alternative, hMSCs could be isolated from the patient and grown in culture. The hMSCs could then be mixed with a biocompatible material such as collagen, collagen sponge, alginate, polylactic acid material etc. to form a composite. The composite would then be treated to induce adipogenic differentiation of the MSCs in vitro for 1–3 weeks, then implanted when needed. For example, adipogenic MSCs could be mixed with a solubilized collagen or other biomaterial which is then allowed to gel to form a three dimensional composite that could be used for breast augmentation following mastectomy. Such a composite could be formed or sculpted to the appropriate size and shape. Another composition includes the culturing of hMSCs on the acellular skin matrix that is currently on the market such as the product by LifeCell Corporation. In this format the cells would be cultured to populate the matrix and then caused to differentiate as described. The matrix with the adipogenic cells could then be cut by the surgeon to fit the site of reconstruction. As an alternative hMSCs could be induced to become adipocytes prior to their introduction into the biocompatible materials. As another alternative, hMSCs in combination with compounds which promote differentiation into adipocytes may be used with a biomatrix as described without culturing for a period of time to induce differentiation whereby differentiation is induced in whole or in part in vivo.

Similar to their use in reconstructive surgery, adipogenic hMSCs will be of use in elective cosmetic surgery in much the same way; to build up underlying tissue below the skin with a composite of autologous cells and biocompatible material.

The invention will be further described with respect to the following examples; however, the scope of the invention is not to be limited thereby. Unless otherwise described percentages and parts are by weight.

Biochemical Markers of Adipocytes

A number of molecules that are specific markers of adipocytes have been described in the literature that will be useful to characterize the adipocytes derived from hMSCs. These include enzymes involved in the interconversion of fatty acids to triglycerides such as stearoyl-CoA-desaturase (SCDI) or the insulin responsive glucose transporter (GLUT4). The product of the ob gene, leptin is a 16,000 molecular weight polypeptide that is only expressed in pre-adipose cells or adipose tissue. The expression of CCAAT enhancer binding protein, C/EBP, has been shown to precede the expression of several markers of adipogenic differentiation and it is thought to play a key role in adipocyte development. Another marker is 422 adipose P2 (422/aP2), a protein whose expression is enhanced during adipocyte differentiation (Cheneval, et al, 1991.). This differentiation pathway is thought also to involve peroxisome proliferation-activated receptor γ2 (PPAR γ2), which is involved in the initiation of transcription of adipocyte genes (Tontonoz, et al, 1994). Studies using these markers and the described methods will allow a more detailed analysis of the lineage progression of mesenchymal stem cell to adipocyte differentiation.

Lipid soluble dyes as markers of adipocyte differentiation

Lipid soluble dyes are available to stain lipid vaculoes in adipocytes. These include Nile Red, Nile Blue, Sudan Black and Oil Red O, among others. Each of these hydrophobic dyes has a propensity to accumulate in the lipid containing vaculoes of the developing adipocytes and can readily identify the adipogenic cells in populations of differentiating MSCS. At least one of these dyes can be used to isolate adipocytes from non-differentiated cells using a fluorescence activated cell sorter (FACS). An example of the use of Nile Red to identify adipogenic hMSCs is shown in FIG. 4.

EXAMPLE 1

Generation of Adipocytes from Human MSCs

Human MSCs are isolated from the red bone marrow of volunteer donors as described in U.S. Pat. No. 5,486,359.

The cells are grown until colonies are well established and at this point the cells are subcultured (1 to 3) or they can be taken to assay for in vitro adipogenesis. For the adipogenesis assay, hMSCs are subcultured into 35 mm tissue culture dishes at 100,000 cells per dish and fed with 2 milliliters normal hMSC Media (Dulbecco's Modified Eagle's Media (DMEM), 10% selected Fetal Bovine Serum (FBS) and antibiotic/antimycotic mixture (1×) (Life Technologies, Inc.)) and cells are maintained at 37° C., 5% $CO_2$ and 90% humidity. The cells are refed with the fresh media every third day and are allowed to multiply and become confluent. The cells are maintained after reaching confluence by refeeding every third day and this time period of post confluence culturing enhances the adipogenic response in the next step (at least out to 14 days). The differentiation into adipocytes is initiated by changing the media to 2 ml of Adipogenic Induction Media (DMEM with 10% fetal bovine serum containing 10 µg/ml insulin (human recombinant, Boehringer Mannheim Corp.), 0.5 mM methyl isobutylxanthine (MIX)(Sigma Chemical Co.), 1 uM dexamethasone (Dex) (Sigma Chemical Co.)). This media is left on the cells for 48 hrs with cells maintained at 37° C., 5% $CO_2$, 90% humidity and is then replaced with Adipogenic Maintenance Media (DMEM containing 10% FBS and 10 µg/ml insulin). The medium is changed every 3–4 days. The hMSCs begin to show small lipid vacuoles in 3–7 days and these enlarge and become more numerous over time, out to at least 30 days. There are several variations that have been successfully tried.

Figure 1B:
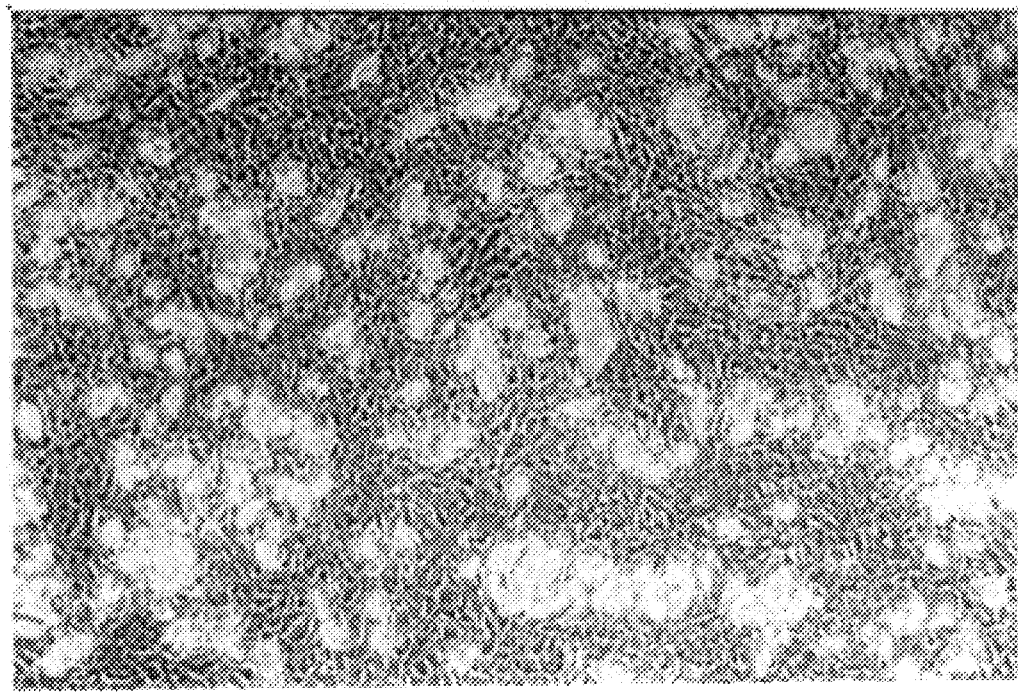
Figure 2A:
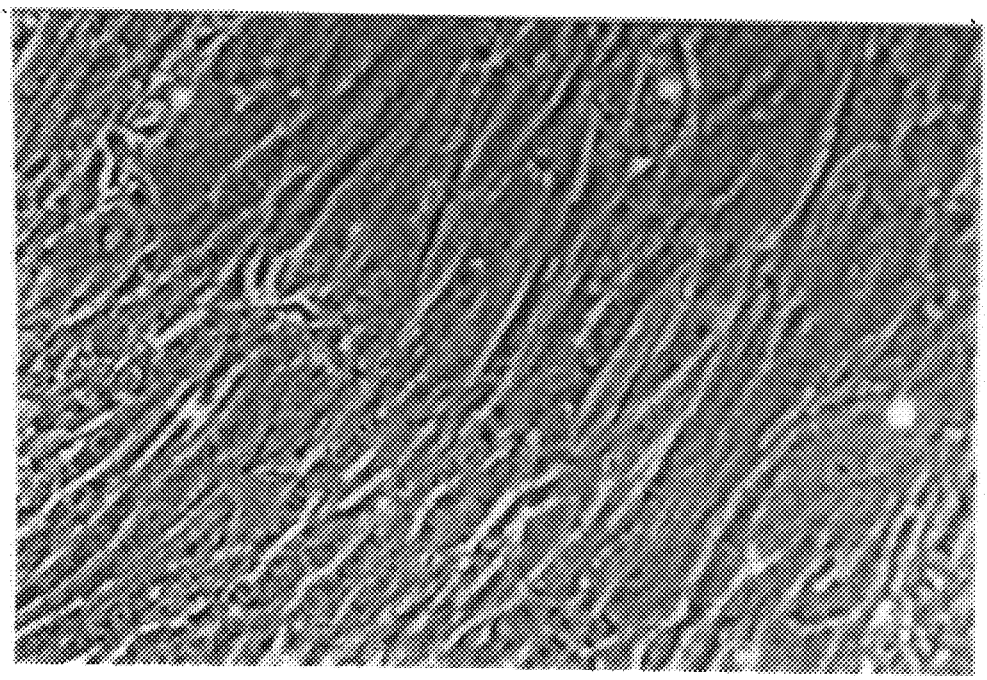
FIG. 2A shows a similar control culture as FIG. 1A at higher magnification (20×).
Figure 2B:
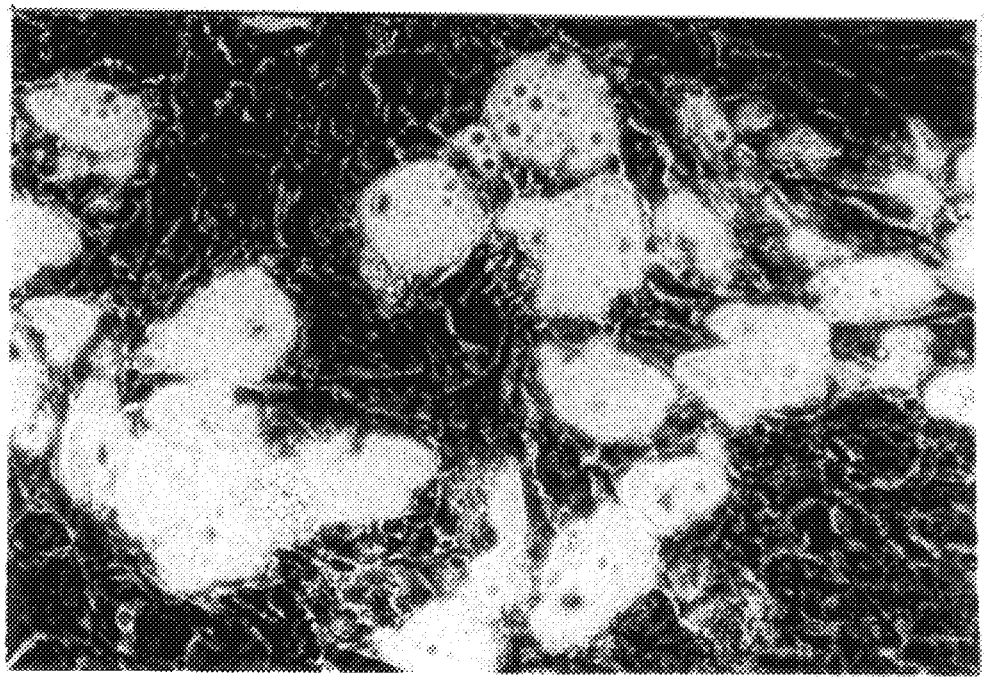
FIG. 2B show a culture of confluent hMSCs that were subjected to Adipogenic Induction media for 48 hours and then maintained in the Adipogenic Maintenance media for 14 days. The many lipid containing vacuoles of adipocytes are evident in a large proportion of the cells.
Figure 3A:
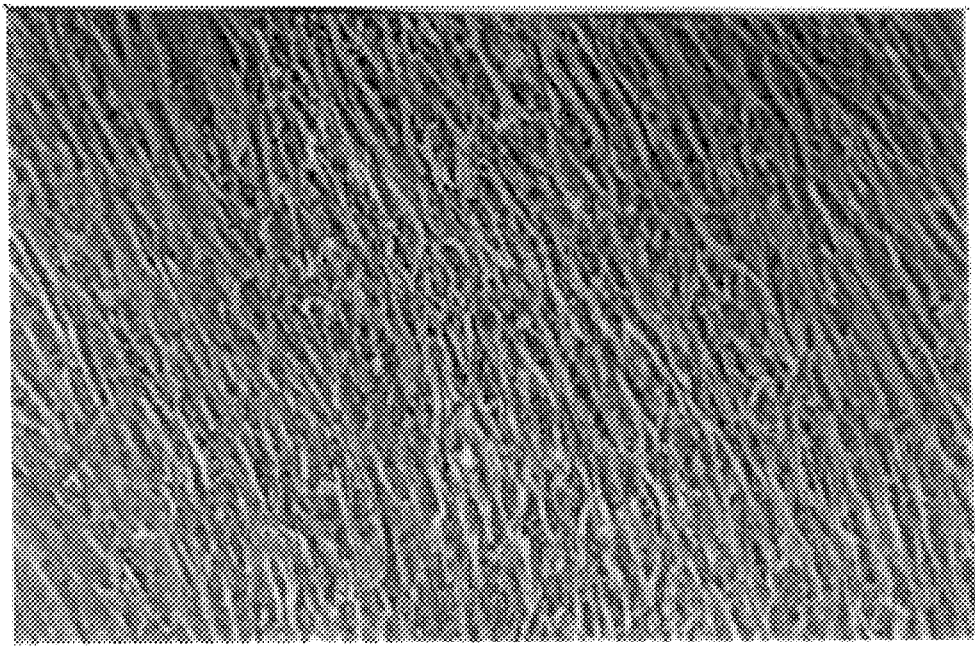
FIGS. 3A–3F show the results of culturing hMSCs under a variety of conditions, only one of which shows a high degree of adipogenic differentiation. All photos are at 10×magnification.
Figure 3B:
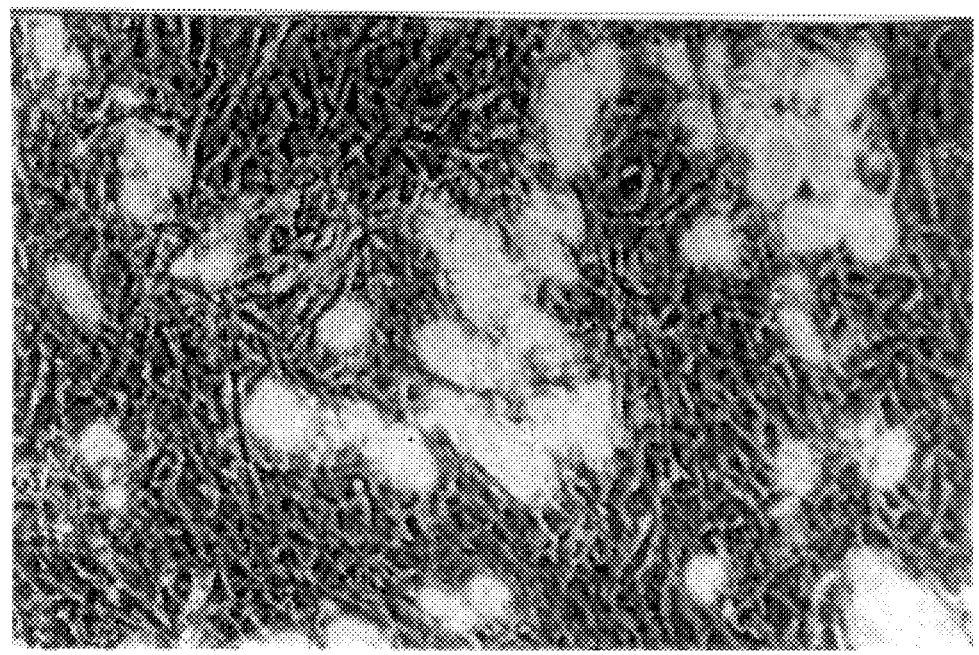
Figure 3C:
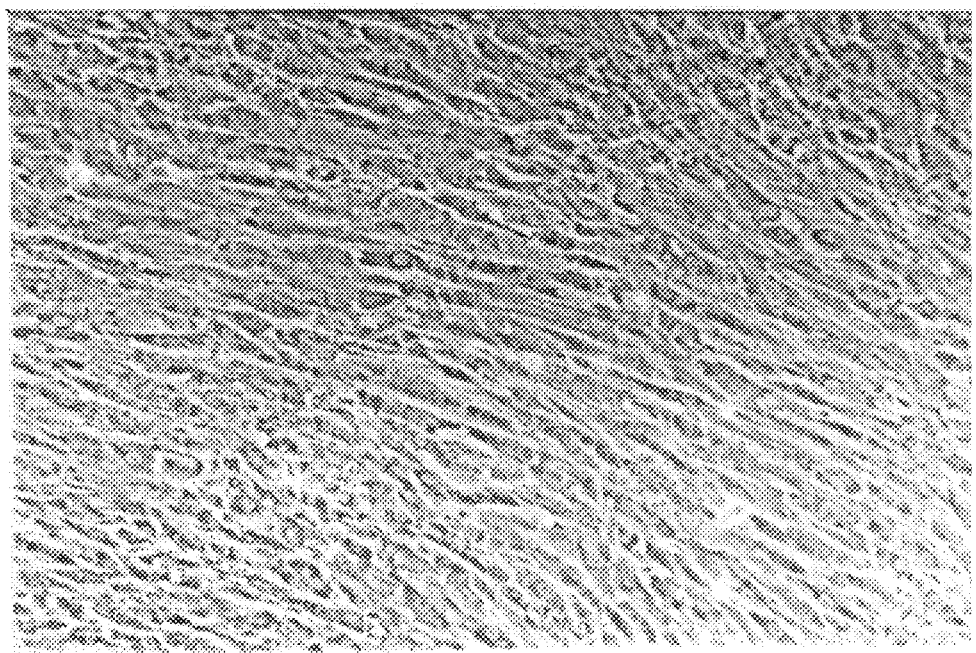
Figure 3D:
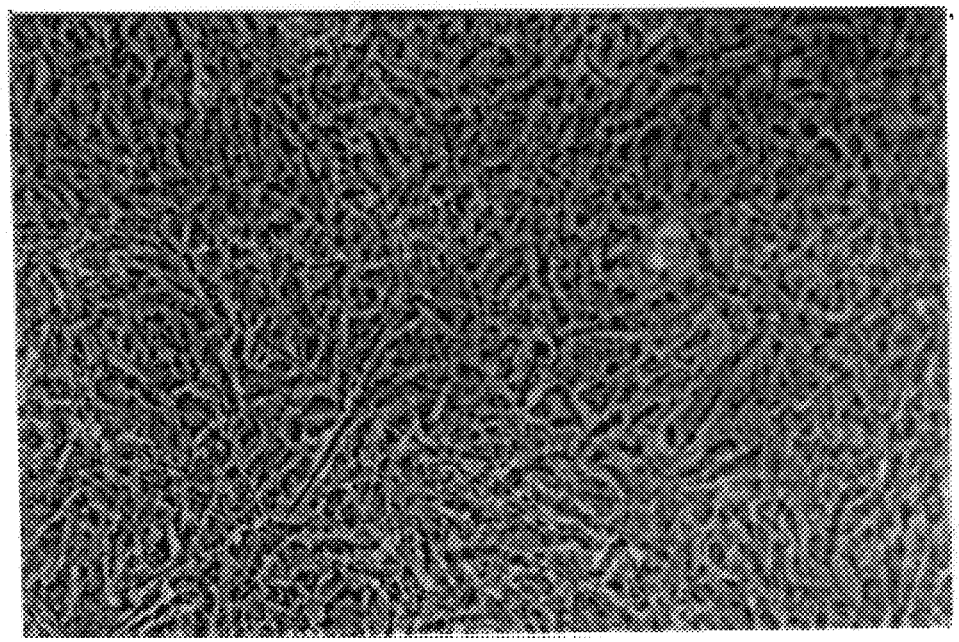
Figure 3E:
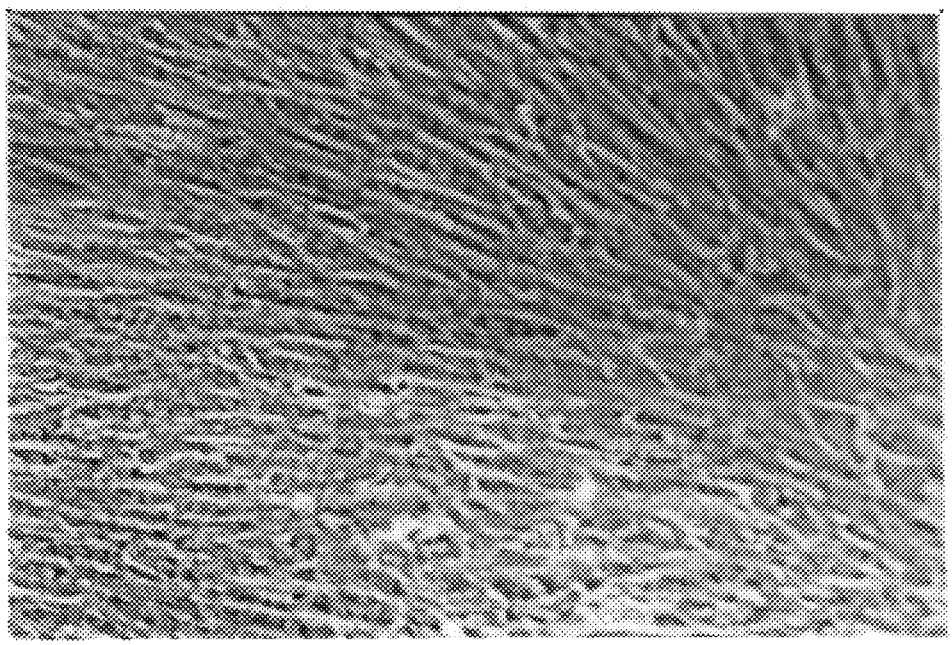
Figure 3F:
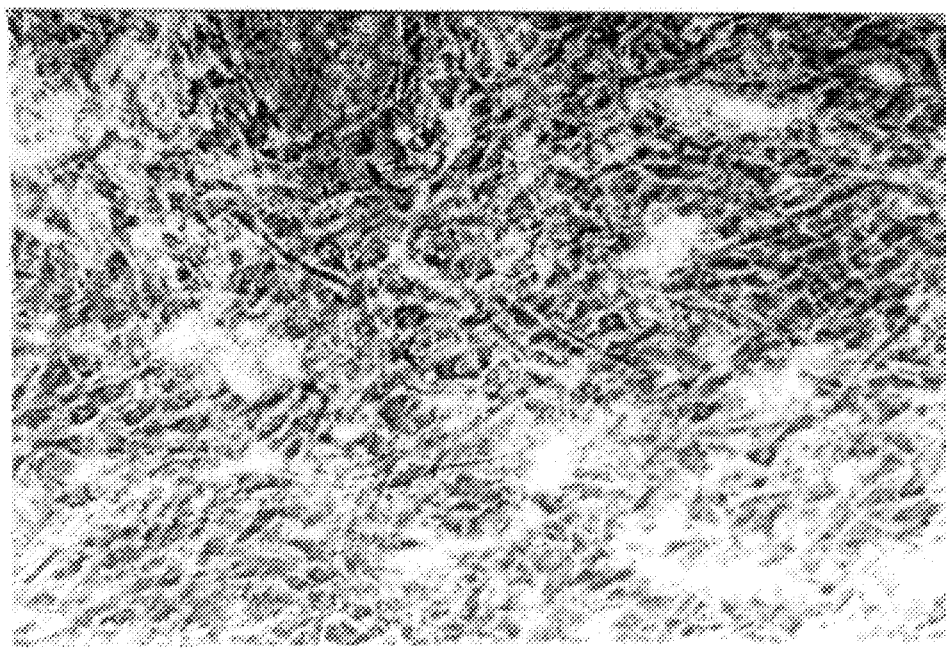

When human MSCs are treated as described above, they undergo differentiation to the adipogenic lineage, as shown in FIG. 1. FIG. 1A shows hMSCs (4×) cultured in normal hMSC media for the same period of time as FIG. 1B. There is no evidence of lipid containing vacuoles and the cells maintain the appearance of fibroblasts at high density. In FIG. 1B are hMSCs that were allowed to become confluent and then maintained for 10 days prior to adding the Adipogenic Induction Media for 48 hrs, and then changed to the Adipogenic Maintenance Media for an additional 2 weeks. The lipid vacuoles are first apparent at about 3–7 days but increase in size and abundance over time. FIG. 2A shows a similar control culture as FIG. 1A at higher magnification (20×). FIG. 2B show a culture of confluent hMSCs that were subjected to Adipogenic Induction Media for 48 hours and then maintained in Adipogenic Maintenance Media for 14 days. The many lipid containing vacuoles of adipocytes are evident in a large proportion of the cells.

FIG. 3 shows the results of culturing hMSCs under a variety of conditions, only one of which shows a high degree of adipogenic differentiation. All photos are at 10×magnification. FIG. 3A shows a culture of hMSCs maintained in normal hMSC culture media with no additives. The cells grow with a fibroblastic morphology. FIG. 3B shows a similar culture that was treated with Adipogenic Induction Media for 48 hours and then with Adipogenic Maintenance Media for an additional 14 days with media changes every 3 days. The adipogenic cells, perhaps as many as 30–35% of the cells, are evident as they contain the large refractile lipid vacuoles. FIG. 3C shows a culture of hMSCs that were maintained in the Adipogenic Maintenance Media for 14 days but was never subjected to the dexamethasone/ methyl isobutylxanthine treatment. The cells maintain a flat morphological appearance with no evident vacuoles. FIG. 3D shows a culture of hMSCs that were treated with normal hMSC media containing 1 µM dexamethasone for 48 hours and then cultured for 14 days in the Adipogenic Maintenance Media. The cells are disorganized but show very few, if any, lipid vacuoles. FIG. 3E shows a culture of hMSCs that was treated with normal hMSC containing 0.5 ml. methyl isobutylxanthine during the induction period and then was maintained for 14 days in the Adipogenic Maintenance Media. The cells retain a flat fibroblastic phenotype. FIG. 3F shows a culture of hMSCs that was treated with a media that induces the cells along a osteogenic pathway. This media contains 0.1 µM dexamethasone, 10 mM µ-glycerol phosphate and 50 µM ascorbic acid 2-phosphate. The presence of refractile osteoid material is evident but no large lipid vacuoles.

Figure 4A:
FIG. 4A shows a culture of hMSCs subjected to the Adipogenic Induction media for 48 hours and then cultured for 14 days in the Adipogenic Maintenance media. The large lipid vacuoles are evident in this bright field image. The lipids can also be revealed by using a fluorescent lipid soluble dye, such as Nile Red, and viewing by epifluorescence illumination as shown in FIG. 4B. Thus, the adipogenic cells can also be identified using vital dyes and histological stains that label the lipid vacuoles.
Figure 4B:
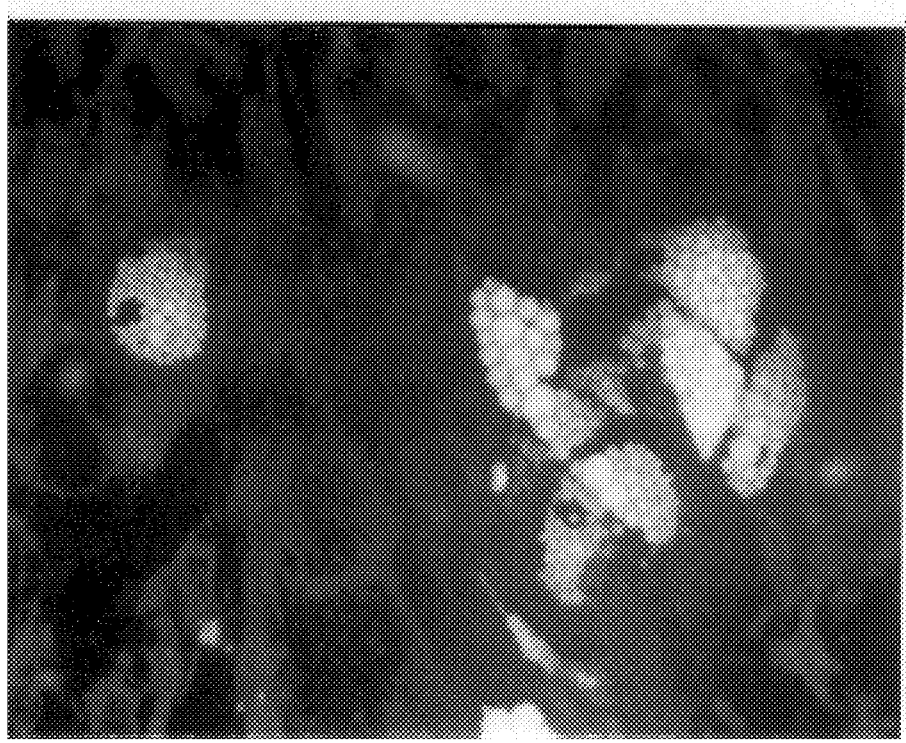

The adipogenic cells can also be identified using vital dyes and histological stains that label the lipid vacuoles. FIG. 4A shows a culture of hMSCs subjected to the adipogenic treatment and cultured for 14 days in the Adipogenic Maintenance Media. The large lipid vacuoles are evident in this bright field image. But the lipids can also be revealed by using a fluorescent lipid soluble dye such as Nile Red (Greenspan, et al. 1985) and viewing by epifluorescence illumination as shown in FIG. 4B.

The results shown here have been reproduced several times with hMSCs derived from different donors and additional information on the method is described here. Similar results have been obtained with hMSCs from all individuals tested (4 or more donors). The percentage of cells that become lipid containing adipocytes varies depending on the specifics of culturing. Specifically, those cells that were allowed to become completely confluent and maintained this way for up to 2 weeks prior to adipocyte induction, showed a much higher percentage of adipocytes overtime than cultures that were induced prior to confluence or at confluence. As many as 30–35% of the hMSCs appear adipogenic at 2 weeks post induction when treated as described herein as shown in FIG. 1B. hMSCs can be cultured in various sizes of culture ware with equal success so obtaining larger numbers of cells should not present any problem.

EXAMPLE 2

Enhancing Adipogenic Differentiation

Figure 5A:
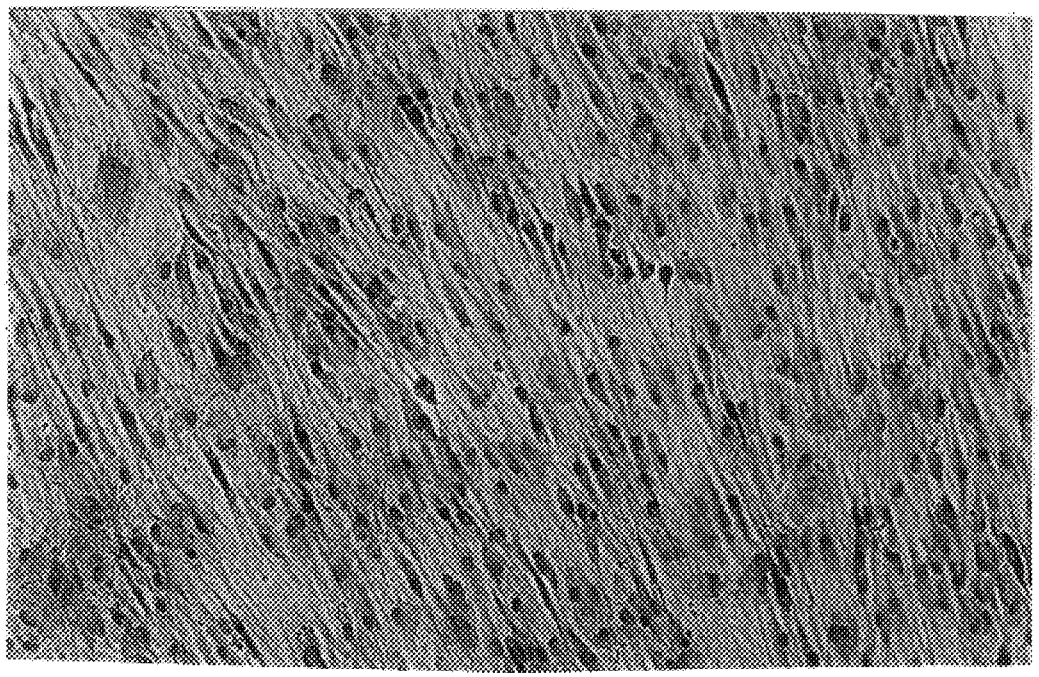
FIG. 5A shows hMSCs in culture which were not treated with Adipogenic Induction media but which were cultured, fixed and stained at the same time as the adipogenic cultures shown in 5B and 5C.
Figure 5B:
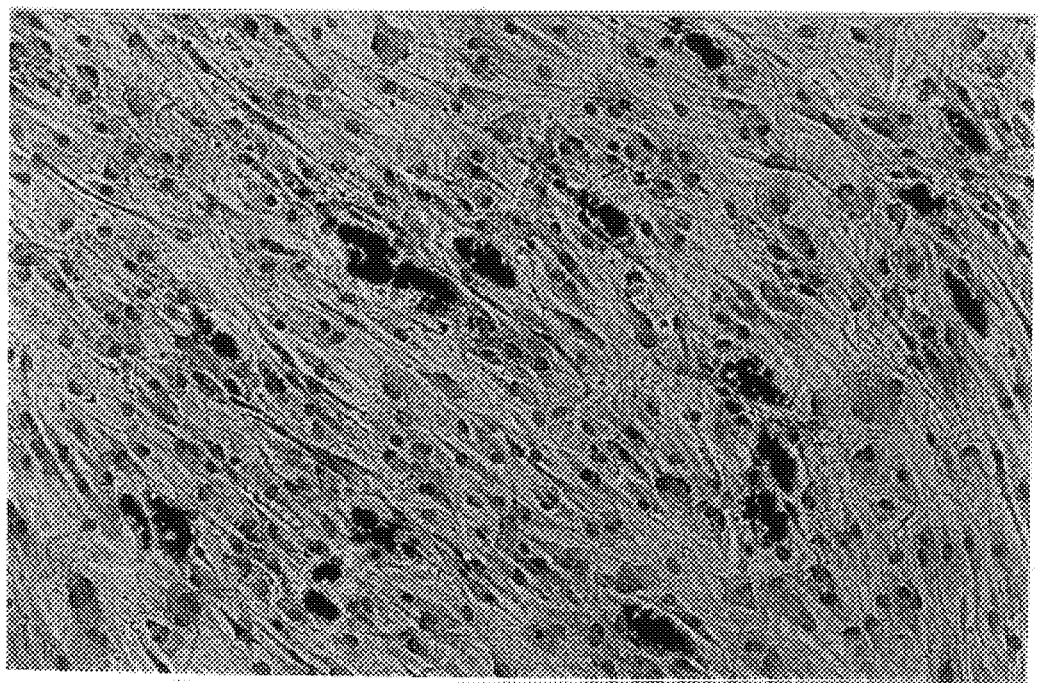
FIG. 5B shows hMSCs that were treated once for 48 hours with Adipogenic Induction media and then cultured for an additional three weeks in Adipogenic Maintenance media and then fixed in neutral buffered formalin and stained with Oil Red O, a lipid soluble dye that accumulates in the fat droplets.
Figure 5C:
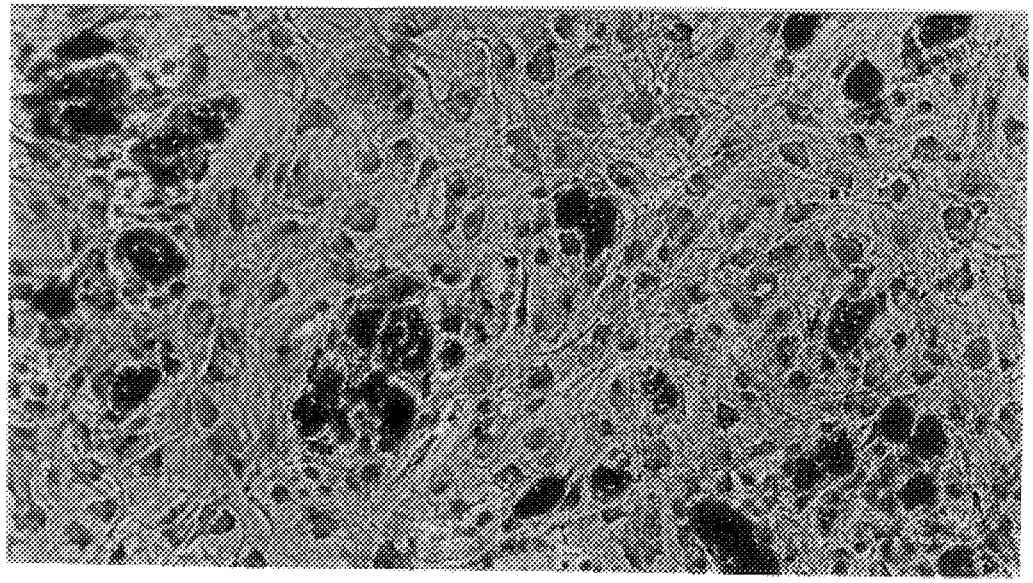
FIG. 5C shows a dish of hMSCs that was retreated with fresh Adipogenic Induction media for a second and third 48 hour period to induce more hMSCs to become adipogenic. As many as 30–40% of the cells were converted to adipocytes by the three induction treatments when viewed two weeks after the third treatment. Panels 5A–5C were all stained with Oil Red O.

These experiments were performed to determine whether a population of human mesenchymal stem cells growing in culture can be treated to induce adipogenic differentiation (which induces a percentage of 5–10% of the cells to become adipocytes), and then retreated at a later time to induce more of the hMSCs to differentiate. Experiments were also performed to examine whether it is possible to purify a population of induced adipogenic cells from the mixed culture of hMSCs and adipogenic MSCs that result from the treatment with adipogenic agents. Both sets of experiments were successful as described below and in the accompanying figures.

hMSCs were induced to the adipogenic phenotype by the culturing in Adipogenic Induction Media for 48 hours as described. The media was then changed to Adipogenic Maintenance Media and cells were cultured at 37° C. in a 5% $CO_2$ atmosphere for 3 to 6 days until there were noticeable lipid droplets visible within cells. Approximately 5–10% of the cells became adipogenic as seen in FIG. 5. FIG. 5A shows hMSCs in culture which were not treated with either adipogenic medium but which were cultured, fixed and stained at the same time as the adipogenic cultures shown in 5B and 5C. FIG. 5B was treated once with Adipogenic Induction Media and then cultured in Adipogenic Maintenance Media for an additional three weeks and then fixed in neutral buffered formalin and stained with Oil Red O, a lipid soluble dye that accumulates in the fat droplets. A dish of hMSCs was also retreated with fresh Adipogenic Induction Media for a second and third 48 hour period to induce more hMSCs to become adipogenic as shown in FIG. 5C. As many as 30–40% of the cells were converted to adipocytes by the three induction treatments when viewed two weeks after the third treatment. Panels 5A–5C were all stained with Oil Red O.

EXAMPLE 3

Isolation of Adipocytes from hMSCs

The generation of adipocytes from human mesenchymal stem cells by the conditions described above produces large numbers of adipocytes, perhaps as many as 30%–40% of the cells present. For uses requiring a pure population, the adipocytes can be isolated from the non-adipogenic hMSCs by several methods as listed below.

Method one for isolating adipogenic hMSCs uses density gradient centrifugation and takes advantage of the greater buoyancy of the lipid-containing adipogenic cells. In this method, cultures containing hMSCs and adipocytes derived from hMSCs are treated with 0.05% trypsin/0.53 mM EDTA to remove the cells from the culture dish and the cells are washed by adding 10 ml of normal hMSC media and centrifuged for 10 minutes at 1000 rpm in the GS-6R centrifuge (Beckman Instruments, Inc.) at 20° C. The pelleted cells containing adipocytes and hMSCs are resuspended in 2 ml of the Adipogenic Maintenance Media and carefully layered on top of 8 ml of Percoll of a density of 1.045 g/ml. The tubes are centrifuged at 2,200 rpm (1100×g) in a Beckman GS-6R centrifuge for 20 minutes at 3° C. The adipocytes are recovered in the uppermost 2 mls and at the interface with the 1.045 density Percoll. (The non-adipogenic MSCs enter into the 1.045 density Percoll and can be recovered at the bottom of the tube.) The recovered adipocytes are washed by addition of 10 mls of the Adipogenic Maintenance Media and centrifuged at 1000 rpm for 10 min at 20° C. in the GS-6R centrifuge. The adipocytes are replated at a density of 150,000 cells per 35 mm dish in Adipogenic Maintenance Media and returned to the incubator.

Method two for isolating adipogenic hMSCs uses fluorescence activated cell sorting (FACS). The hMSCs differentiating into adipocytes in a culture can be isolated by using a lipid soluble fluorescent dye, such as Nile Red (10–100 ug/ml) to stain lipid vacuole-containing adipocytes. The culture is then treated with trypsin/EDTA as above to release the cells from the culture vessel and subjecting the mixed population to fluorescence activated cell sorting (FACS). The parameters on the machine are adjusted to select and recover adipogenic cells in the population and they can be used directly or replated and cultured in the incubator.

As described below, Method three of isolating the adipogenic cells in a mixed population is to trypsin/EDTA treat and wash the cells as above. The cells are then placed in a tissue culture flask and the flask is filled with media. The flask is closed tightly and turned upside-down so that the surface treated for cell adhesion is uppermost. The buoyant, lipid-droplet-containing adipocytes rise to top and attach to the surface of the flask. The next day the media is removed and the flask rinsed with fresh media and the flask turned right-side-up. The flask, now with only enough media to cover the cell layer, is returned to the incubator for further maintenance.

Figure 6A:
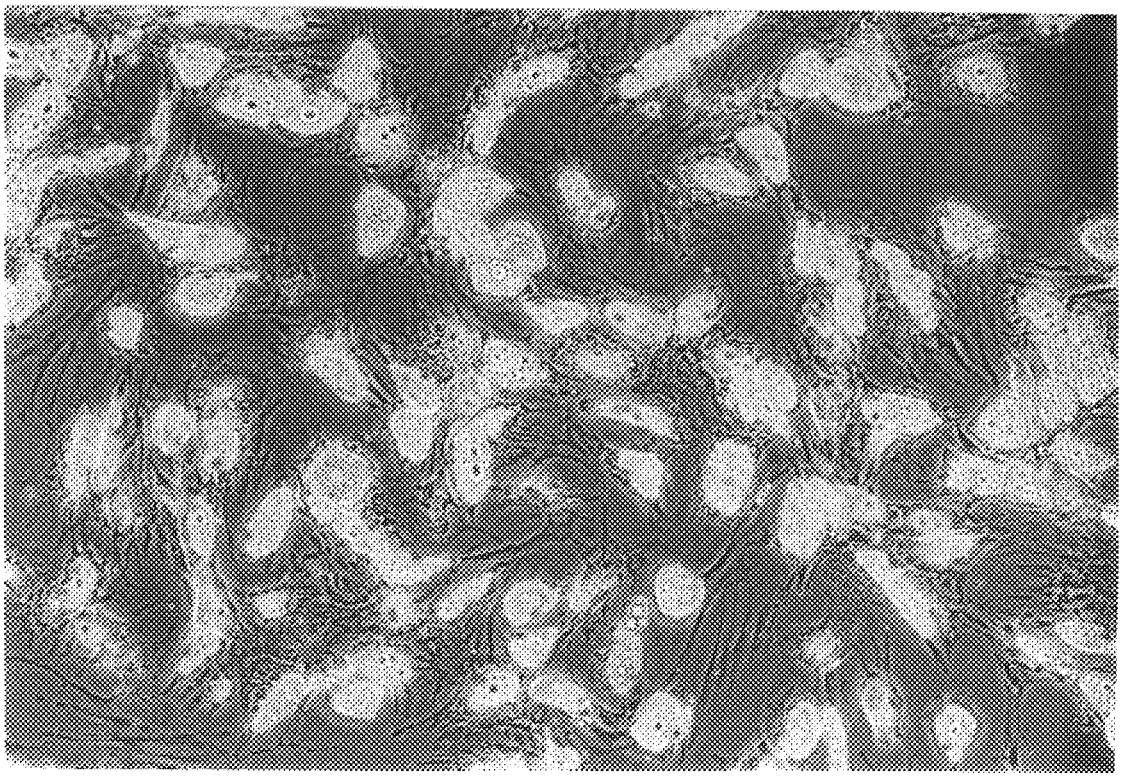
FIG. 6A shows the isolated adipogenic hMSCs that attached to the uppermost surface. The population is composed of greater than 99% adipogenic cells as evidenced by the lipid droplets in every cell.
Figure 6B:
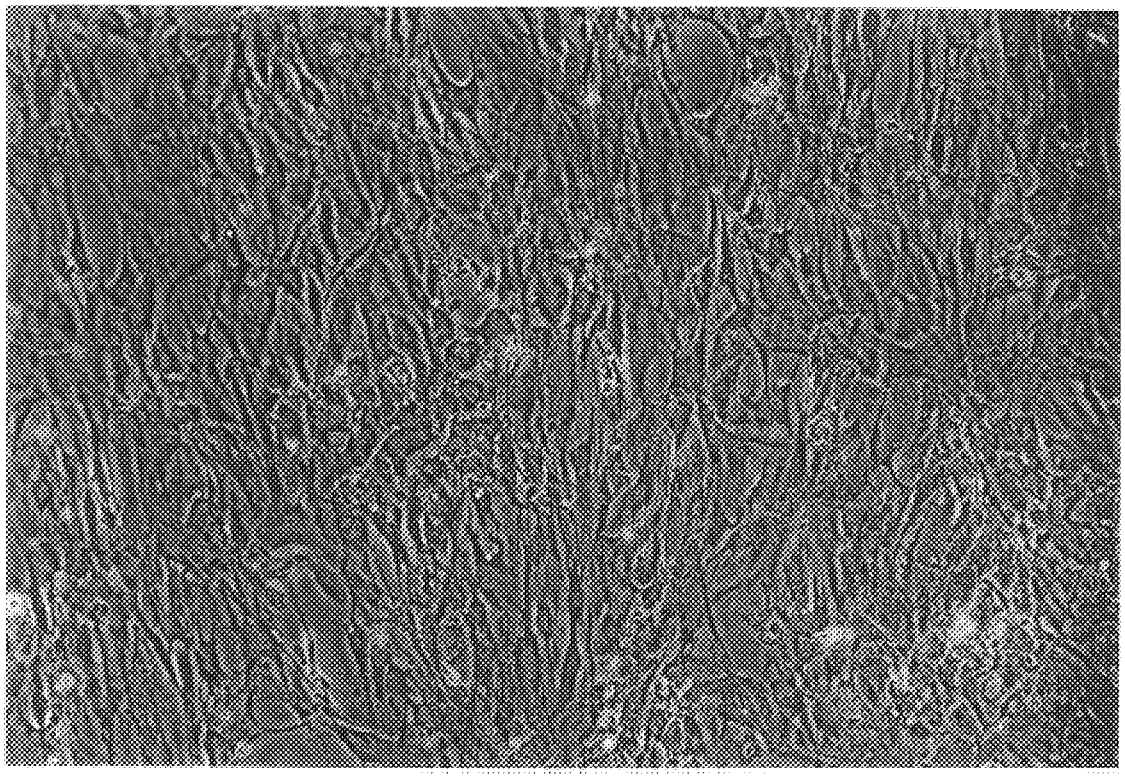
FIG. 6B shows the non-adipogenic hMSCs that settled to the lower surface of the flask. Very few cells containing lipid droplets were present on the lower surface. These non-adipogenic cells could be treated with trypsin/EDTA and replated to another dish and be shown to retain adipogenic potential (data not shown), indicating that they remain as mesenchymal stem cells, capable of lineage progression.

Adipogenic hMSCs accumulate lipid droplets which decreases the bouyant density of the cells. The adipogenic hMSCs were then isolated as follows. The dish of cells containing adipocytes and non-adipogenic hMSCs from a culture that were treated for only one 48 hr induction period and then grown for three weeks, was treated with 0.05% trypsin and 5 mM EDTA for 3–5 minutes to release the cells from the dish. The cells were then rinsed from the dish with 10 ml of fresh media and placed in a 25 cm² flask and the flask was filled to the brim with fresh media. The flask was turned upside down so the usual culture surface was uppermost and the flask placed in the 37° C. incubator overnight. The more bouyant adipogenic cells rose to the top and attached to the surface, while the non-adipogenic hMSCs settled to the bottom surface and attached. The following day photos were taken of the cells on each surface as shown in FIG. 6. FIG. 6a shows the adipogenic hMSCs that attached to the uppermost surface. The population is composed of greater than 99% adipogenic cells as evidenced by the lipid droplets in every cell. FIG. 6b shows the non-adipogenic hMSCs that settled to the lower surface of the flask. Very few cells containing lipid droplets were present on the lower surface. These non-adipogenic cells could be treated with trypsin/EDTA and replated to another dish and be shown to retain adipogenic potential (data not shown), indicating that they remain as mesenchymal stem cells, capable of lineage progression.

CITED LITERATURE

MacDougald, O. A., C-S. Hwang, H. Fan, and M. D. Lane. 1995. Regulated expression of the obese gene product (leptin) in white adipose tissue and 3T3-L1 adipocytes. PNAS 92:9034–9037.

Hwang, C-S., S. Mandrup, O. A. MacDougald, D. E. Geiman and M. D. Lane. 1996. Transcriptional activation of the mouse obese (ob) gene by CCAAT/enhancer binding protein α. PNAS 93:873–877.

Cornelius, P., O. A. MacDougald and M. D. Lane. 1994. Regulation of adipocyte development. Annu. Rev. Nutrition 14:99–129.

Yeh, W-C., Z. Cao, M. Classon and S. L. McKnight. 1995. Cascade regulation of terminal adipocyte differentiation by three members of the C/EBP family of leucine zipper proteins. Genes and Development 9:168–181.

Freytag, S. O., and T. J. Geddes. 1992. Reciprocal regulation of adipogenesis by Myc and C/EBPα. Science 256:379–382.

Bortell, R., T. A. Owen, R. Ignotz, G. S. Stein and J. L. Stein. 1994. TGFO, prevents the down-regulation of type I procollagen, fibrinectin, and TGFO, gene expression associated with 3T3-L1 pre-adipocyte differentiation. J. Cellular Biochem. 54:256–263.

Sadowski, H. B., T. T. Wheeler and D. A. Young. 1992. Gene expression during 3T3-L1 adipocyte differentiation. J. Biological Chem. 266:4722–4731.

Flier, S. J. 1995. The adipocyte:storage depot or node o the energy information superhighway. Cell 80:15–18.

Greenspan, P., E. P. Mayer and S. D. Fowler. 1985. Nile red: A selective fluorescent stain for intracellular lipid droplets. J. Cell Biology 100:965–973.

Smith, M. J. and W. Wharton. 1992. Differentiation of A31T6 proadipocytes to adipocytes: A flow cytometric analysis. Exper. Cell Research 199:29–38.

Gimble, J. M., K. Youkhana, X. Hua, H. Bass, K. Medina. 1992. Adipogenesis in a myeloid supporting bone marrow stroma cell line. J. Cell. Biochem. 50:73–82.

Pietrangell, C. E., S-1. Hayashi and P. W. Kincade. 1988. Stromal cell lines which support lymphocyte growth: characterization, sensitivity to radiation and responsiveness to growth factors, Europ. J. Immunolgy. 18:863–872.

Chehab, F. F., M. E. Lim and R. Lu. 1996. Correction of the sterility defect in homozygous obese female mice by treatment with the human recombinant leptin. Nature Genetics 12 318–320.

Beresford, J. N., J. H. Bennett, C. Devlin, P. S. Leboy and M. E. Owen. 1992. Evidence for an inverse relationship between the differentiation of adipocytic and osteogenic cells in rat marrow stromal cell cultures. J. Cell Science 102:341–351.

Bortell, R. T. A. Owen, R. Ignotz, G. S. Stein and J. L. Stein. 1994. TGF $\beta_1$ prevents the down regulation of type I procollagen, fibrinectin, and TGF $\beta_1$ geneexpression associated with 3T3-L1 pre-adipocvte differentiation. J. Cellular Biochem. 54:256–263.

Gimble, J. M., C. Morgan, K. Kelly, X. Wu, V. Dandapani, C.-S. Wang and V. Rosen. 1995. Bone Morphogenetic Proteins inhibit adipogenic differentiation by bone marrow stromal cells. J. Cellular Biochemistry 58:393–402.

Grigoriadis, A. E., J. N. M. Heersche and J. E. Aubin. 1988. Differentiation of muscle, fat, cartilagem and bone from progenitor cells present in a bone derived clonal cell population: effect of dexamethasone. J. Cell Biology 106:2139–2151.

Ibid., 1990. Continuosly growing bipotential and monopotential and chondrogenic subclones isolated from the multipotential RCJ 3.1 clonal cell line. Developmental Biology 142:313–318.

Umezawa, A., K. Tachlbana, K. Harigaya, S. Kusakarl, S. Kato, Y. Watanabe and T. Takano. 1991. Colony stimulating factor I expression is down-regulated during the adipocyte differentiation of H-1/A marrow stromal cells and induced by cachetin/tumor necrosis factor. Mol. Cell. Biol. 11:920–927.

Yamaguchi, A. and A. J. Kahn. 1991. Clonal osteogenic cell lines express myogenic and adipocytic developmental potential. Calcified Tissue International 49:221–225.

Cheneval, D. R. J. Christy, D. Geiman, P. Cornelius, and M. D. Lane, 1991. Cell-free transcription directed by the 422 adipose P2 gene promoter: activation by the CCAAT/enhancer bindind protein. Proc. National Academy of Sciences USA 88:8465 69.

Ingalls, A. M., M. M. Dickie and G. D. Snell. 1950, Obese, a new mutation in the house mouse, J. Heredity 41:371–318.

Tontonoz, P. E., Hu, and B. M. Spiegelman. 1994. Stimulation of adipogenesis in fibroblasts by mPPARγ2, a lipid activated transcription factor. Cell 79:1147–1156.

Konieczny, S. F. and C. P. Emerson. 1984. 5-azacytidine induction of stable mesodermal stem cell lineages from 10T1/2 cells: evidence for regulatory genes controlling differentiation. Cell 38:791–800.

Spiegelman, B. M. and H. Green. 1980. Control of specific protein biosynthesis during the adipose conversion of 3T3 cells. J. Biol. Chem. 255:8811–8818.

Zhang, Y. et al. 1994. Nature 372:425–432.

MacDougald. O. A. and M. D. Lane 1995. Transcriptional Regulation of gene expression during adipocyte differentiation. Annu. Rev. Biochem. 64:345–373.

What is claimed is:

1. A composition which comprises mesenchymal stem cells which have been isolated from a human and which have potential to differentiate into cells of more than one connective tissue type and a substance in an amount effective to induce said stem cells to differentiate into the adipogenic lineage.

2. The composition of claim 1 wherein the substance which induces cells from the mesenchymal stem cell population to differentiate into the adipogenic lineage comprises a glucocorticoid and a compound which elevates intracellular levels of cAMP.

3. The composition of claim 2 wherein the glucocorticoid is selected from the group consisting of dexamethasone, hydrocortisone, and cortisone.

4. The composition of claim 2 wherein the substance which elevates intracellular cAMP is selected from the group consisting of dibutyryl-cAMP, 8-CPT-cAMP (8-(4) chlorophenylthio)-adenosine 3', 5' cyclic monophosphate; 8-bromo-cAMP; dioctanoyl-cAMP and Forskolin.

5. The composition of claim 2 wherein the substance which induces cells from the mesenchymal stem cell population to differentiate into the adipogenic lineage further comprises insulin.

6. A process for inducing human mesenchymal stem cells to differentiate into adipocytes, comprising:

contacting human mesenchymal stem cells with (i) a glucocorticoid and (ii) a compound which elevates intracellular levels of cAMP, said glucocorticoid and said compound which elevates intracellular levels of cAMP being employed in an amount sufficient to induce human mesenchymal stem cells to differentiate into adipocytes.

7. The process of claim 6 which further comprises isolating the adipocytes from remaining hMSCs.

8. The composition of claim 1 wherein the substance which induces cells from the mesenchymal stem cell population to differentiate into the adipogenic lineage comprises a glucocorticoid and a compound which inhibits degradation of cAMP.

9. The composition of claim 8 wherein the substance which inhibits degradation of cAMP is a phosphodiesterase inhibitor selected from the group consisting of methyl isobutylxanthine, theophylline, caffeine, and indomethacin.

10. The composition of claim 8 wherein the substance which induces cells from the mesenchymal stem cell population to differentiate into the adipogenic lineage further comprises insulin.

11. The process of claim 10 which further comprises isolating the adipocytes from remaining hMSCs.

12. The process of claim 10 wherein (ii) is a phosphodiesterase inhibitor.

13. The process of claim 12 wherein (i) and (ii) are in admixture with each other.

14. A process for inducing human mesenchymal stem cells to differentiate into adipocytes, comprising:

contacting human mesenchymal stem cells with (i) a glucocorticoid and (ii) a compound which inhibits degradation of cAMP, said glucocorticoid and said compound which inhibits degradation of cAMP being employed in an amount sufficient to induce human mesenchymal stem cells to differentiate into adipocytes.

* * * * *

UNITED STATES PATENT AND TRADEMARK OFFICE
CERTIFICATE OF CORRECTION

PATENT NO. : 5,827,740
DATED : October 27, 1998
INVENTOR(S) : Mark F. Pittenger

It is certified that error appears in the above-identified patent and that said Letters Patent is hereby corrected as shown below:

In the claims, Column 14:

Line 9, replace "11" with --12-- and replace "10" with --11--.

Line 11, replace "12" with --13-- and replace "10" with --11--.

Line 13, replace "13" with --14-- and replace "12" with --13--.

Line 15, replace "14" with --11--.

Signed and Sealed this

Fourth Day of May, 1999

Attest:

Attesting Officer

Q. TODD DICKINSON

Acting Commissioner of Patents and Trademarks